United States Patent
Fattori et al.

(10) Patent No.: US 7,117,555 B2
(45) Date of Patent: *Oct. 10, 2006

(54) TOOTHBRUSH WITH MOVABLE HEAD SECTIONS FOR ENHANCED ORAL CARE

(75) Inventors: Joseph Edward Fattori, Mendham, NJ (US); John J. Gatzemeyer, Hillsborough, NJ (US); Eyal Eliav, New York, NY (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/218,993

(22) Filed: Sep. 2, 2005

(65) Prior Publication Data

US 2006/0000039 A1   Jan. 5, 2006

Related U.S. Application Data

(63) Continuation of application No. 10/198,260, filed on Jul. 17, 2002, now Pat. No. 6,938,294.

(51) Int. Cl.
*A61C 17/34* (2006.01)
(52) U.S. Cl. .................. 15/22.2; 15/28; 15/22.1
(58) Field of Classification Search ............ 15/22.1, 15/22.2, 28
See application file for complete search history.

(56) References Cited

U.S. PATENT DOCUMENTS

| | | | |
|---|---|---|---|
| 2,140,307 A | 12/1938 | Belaschk et al. | |
| 5,259,083 A | 11/1993 | Stansbury, Jr. | |
| 5,504,958 A | 4/1996 | Herzog | |
| 5,524,312 A * | 6/1996 | Tan et al. | 15/22.1 |
| 5,625,916 A | 5/1997 | McDougall | |
| 6,000,083 A | 12/1999 | Blaustein et al. | |
| 6,148,462 A * | 11/2000 | Zseng | 15/22.1 |
| 6,434,773 B1 | 8/2002 | Kuo | |
| 6,574,820 B1 | 6/2003 | DePuydt et al. | |
| 6,725,490 B1 | 4/2004 | Blaustein et al. | |
| 6,785,929 B1 | 9/2004 | Fritsch et al. | |
| 2003/0066145 A1 | 4/2003 | Prineppi | |
| 2003/0084526 A1 | 5/2003 | Brown et al. | |
| 2003/0182744 A1 | 10/2003 | Fattori et al. | |
| 2003/0196283 A1 | 10/2003 | Eliav et al. | |

FOREIGN PATENT DOCUMENTS

| | | |
|---|---|---|
| GB | 2 317 555 | 9/1996 |
| JP | 10-66704 | 3/1998 |
| WO | WO 02/05725 | 1/2002 |

* cited by examiner

*Primary Examiner*—Gladys J P Corcoran
*Assistant Examiner*—Shay L. Balsis
(74) *Attorney, Agent, or Firm*—Ellen K. Park

(57) ABSTRACT

The present invention relates to a powered toothbrush with two moving bristle bearing parts, the first such part is disc-shaped and rotates or oscillates back-and-forth, the second such part is coupled to the brush head by an elastomeric material, such that the second section can be moved either by the force of brushing or by selective engagement with the drive mechanism of the toothbrush.

11 Claims, 7 Drawing Sheets

TOOTHBRUSH WITH MOVABLE HEAD SECTIONS FOR ENHANCED ORAL CARE

This is a continuation of U.S. application Ser. No. 10/198,260, filed Jul. 17, 2002, now U.S. Pat. No. 6,938,294 which is incorporated by reference in its entirety in this present application.

FIELD OF THE INVENTION

The present invention relates to powered toothbrushes, and more particularly, to a toothbrush having a head with two distinct moving sections that each provides enhanced cleaning and/or massaging oral health benefits to the soft and hard tissues of the mouth.

DISCUSSION OF RELATED ART

Toothbrushes provide many oral hygiene benefits, including for example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles mounted on the brush head, which bristles move at much higher speeds than possible with manual motivation alone. They also may impart different types and directions of motion. These motions, generally in combination with manual movement of the toothbrush by the user, provide superior cleaning than manual toothbrushes. Typically, powered toothbrushes are powered by disposable or rechargeable batteries that power an electric motor that in turn drives the toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw, and each row of teeth consequently has a convex outer curve and a concave inner curve. Individual teeth often have extremely complex surfaces, with areas that may be flat, concave, or convex. The more precise conformation between the bristles and the tooth surface, the more effective the toothbrush may be in cleaning, whitening and/or stimulating.

Known powered toothbrushes typically arrange the bristles in a compact conical or cylindrical pattern on a generally circular, disk-shaped bristle carrier. The powered toothbrush heads are traditionally compact, generally oval in shape and the heads are produced with a flat trimmed bristle pattern. Alternatively, other head shapes and bristle patterns are available.

One example of a powered toothbrush is depicted in U.S. Pat. No. 5,625,916 to McDougall, which is hereby incorporated by reference in its entirety. The toothbrush shown in McDougall has a disc-shaped bristle carrier. The bristle carrier, and thus the bristles, are driven in a vibrating or oscillating manner. This type of toothbrush is described herein with reference to FIGS. 1A–1C. A toothbrush 5 includes a handle portion 10 at a proximal end of the toothbrush 5 and a head 11 at a distal end of the toothbrush 5. The handle portion 10 has compartments for containing a powered motor 14 and batteries 15 and 16. The head 11 includes a generally circular bristle holder (carrier) 13. A rotatable shaft 12 extends from the motor 14 to the head 11. A shaft coupling 17 may be located along the shaft 12 and configured to provide for the shaft 12 to be separated at a point between the motor 14 and the head 11. This permits the shaft to be removed from the toothbrush 5, e.g., for cleaning, servicing, or replacement.

As disclosed in McDougall, the head 11 includes a post 18 that provides a rotational pivot axis for the bristle holder 13 containing bristle tufts 19. The distal end of the shaft 12 has a journal or offset 20 that is radially displaced from the longitudinal axis of the shaft 12, which may be integrally formed therewith. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages the slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Although powered toothbrushes such as those described immediately above provide advantages over manual toothbrushes, they are subject to various limitations. A rotating or oscillating bristle holder (carrier) with a typical disc-shaped bristle carrier provides significantly less bristle area for teeth cleaning than a conventional oblong or oval manual toothbrush for enhanced cleaning and whitening. Also, when the bristles are placed in contact with the teeth during brushing, there is less bristle contact with adjacent areas, such as the gums for stimulation thereof.

One attempt to overcome the limitations associated with a small powered bristle area is shown in U.S. Pat. No. 6,000,083 to Blaustein et al. The toothbrush in Blaustein et al. has a bristle area and pattern similar to a manual toothbrush, but an area of the bristles has simply been replaced by a powered bristle section. The result is that the head has a powered or moving bristle section and static bristle section. The limitation of Blaustein et al. is that the static bristle section provides no better cleaning, whitening or stimulation than a manual toothbrush.

International Application No. PCT/EP01/07615 of Braun GmbH discloses a powered toothbrush with two separate bristle parts that can move. Each bristle part can have a different range and/or type of motion. However, only one bristle part is powered. The other unpowered bristle part moves due to a resonance effect imparted by the frequency of the movement of the first bristle part.

Providing the free resonance effect disclosed in the Braun PCT application inherently has a number of problems. First, any contact between the bristle parts will dampen or cancel the resonance of the unpowered bristle part, the unpowered bristle part "floats" separately from the powered bristle part. This necessitates separation or gaps between the unpowered bristle part and the remainder of the brush head, which gaps expose the internal workings of the head to entry and accumulation of foreign matter such as water, saliva, toothpaste, and food particles. This foreign matter accumulation may interfere with the workings of the unpowered bristle head and interfere with its function. In addition, food particles may remain in the head and may fester and host microorganisms, which are undesirable if not potentially harmful when the head is re-introduced into the mouth.

Another limitation of the design disclosed in the Braun PCT application is that movement of the unpowered bristle part may be damped by contact with the teeth, or lessened when the frequency of the powered part shifts from the resonance frequency. This can occur due to pressure imparted against the powered bristle part by the teeth or gums during brushing. Finally, the energy imparted to the unpowered bristle part is only a portion of the energy input into the powered part. Therefore, the unpowered bristle part is less effective in cleaning than the powered part, limiting the overall effectiveness of the toothbrush.

Thus, there is a need in the art for a powered toothbrush with increased effectiveness through a larger area of powered or driven bristles or bristles that are otherwise movable. There is also a need for a toothbrush having enhanced cleaning, whitening and/or stimulation than known toothbrushes. There is further a need for such improved toothbrushes to be comparable in manufacturing and purchasing costs as known powered toothbrushes.

SUMMARY OF THE INVENTION

A powered toothbrush is provided and includes a handle portion at a proximal end and a head at a distal end with a neck being formed between the handle portion and the head. According to one embodiment, the head has two distinct movable parts or sections that provide oral health benefits since each is adapted to have a number of bristles or elastomeric cleaning members extending therefrom to contact surfaces of the teeth and surrounding areas. The toothbrush has a drive mechanism that imparts movement to the two movable parts to deliver a cleaning, polishing, whitening action that supplements the cleaning efficiency of a typical powered toothbrush with single a disc-shaped bristle carrier.

In one embodiment, the first moving head part is a first disc-shaped bristle carrier that supports a number of bristle tufts, elastomeric cleaning members, or a combination thereof. The first bristle carrier is operatively mounted to the head and is coupled to the drive mechanism such that the first bristle carrier rotates or oscillates back and forth in a direction generally parallel to the toothbrush head. Preferably, the first bristle carrier is oscillated back and forth in a rotational direction. The second movable part is in the form of a second bristle carrier which is supported and coupled to the head by an elastomeric member. This combination of a powered movement of the first bristle carrier to scrub away plaque and debris from the teeth and a second bristle carrier which moves in use is preferred, as the second bristle carrier will yield during brushing to reduce the pressure being applied by the bristles extending from the second bristle carrier on the gums and other oral soft tissues and further, the bristles extending from the second bristle carrier will be continuously realigned during brushing accommodate to the curvature of the dentiture. Further, by only having one powered movable part, the size of the motor and drain on the preferred battery power source is reduced, providing economic savings.

In a second embodiment of the present invention, the elastomeric supported bristle carrier may be selectively engaged by the drive mechanism to vibrate or oscillate in a direction generally perpendicular to the head, thereby providing a brush head with an extended field of cleaning elements that provides at least two different types of bristle motion for enhanced cleaning, whitening and/or massaging of the dental tissues. In a preferred alternative of this second embodiment, a single drive shaft is utilized for rotationally oscillating the first bristle carrier and also for causing the second bristle carrier to vibrate or oscillate in-and-out in a direction generally perpendicular to the direction of movement of the oscillating first bristle carrier.

Other features and advantages of the present invention will be apparent from the foregoing detailed description when read in conjunction with the accompanying drawings.

BRIEF DESCRIPTION OF THE DRAWINGS

The foregoing and other features of the present invention will be more readily apparent from the following detailed description and drawings of illustrative embodiments of the invention in which.

DETAILED DESCRIPTION OF THE PREFERRED EMBODIMENT

Figure 1A:
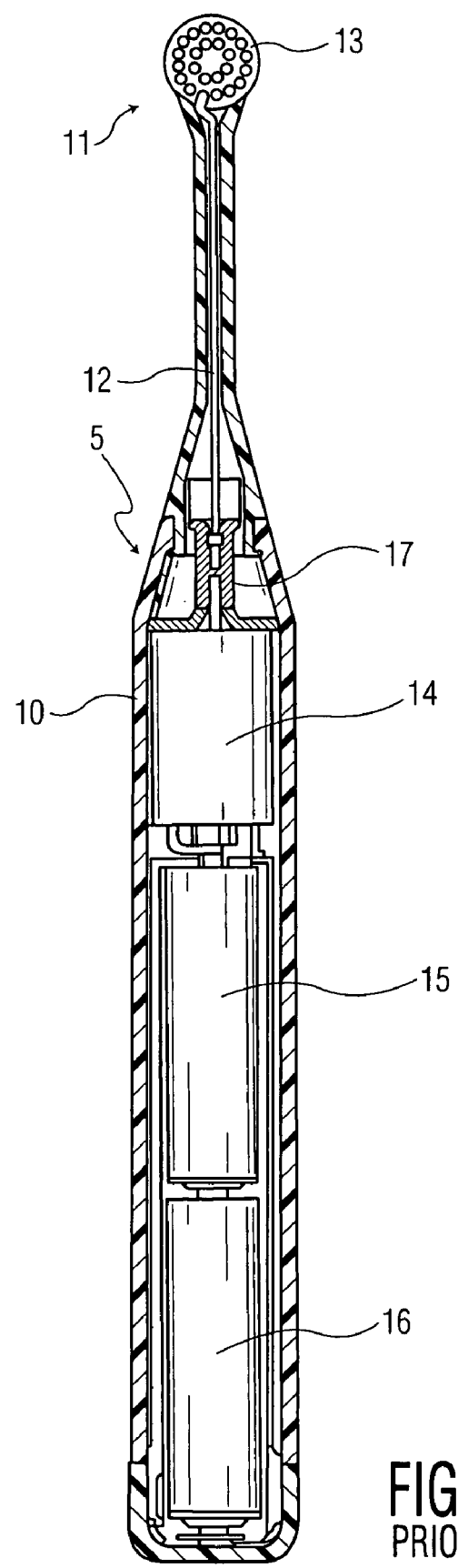
FIG. 1A is a front cross-sectional view of a conventional powdered toothbrush including a head.

Referring first to FIGS. 2 through 7 in which an exemplary powered toothbrush according to a first embodiment is illustrated and generally indicated at 100. The toothbrush 100 includes a handle 102 at a proximal end that defines an interior compartment (not shown) for housing various toothbrush components, including the motor and battery power source, and a brush section 104 that is defined by a neck 106 that terminates in a head 120 at a distal end of the toothbrush 100. The handle 102 has a free proximal end 108 and an opposite, distal neck end 110. The neck 106 generally extends from a first end 112 to a second end 114 with the first end 112 being located at the neck end 110 of the handle 102 and the second end 114 being located at the head 120. In other words, the neck 106 is the portion of the toothbrush 100 that extends between the handle 102 and the head 120. The neck 106 also defines an interior compartment (not shown) for housing various working components of the toothbrush 100, such as a drive shaft. The head 120 is preferably generally aligned with the longitudinal axis of the toothbrush 100 for simplicity of construction, though it can be angled thereto to provide an ergonomic positioning of the brush head with respect to the handle when the brush in use.

According to one embodiment, the neck 106 and the handle 102 are constructed as a unitary member by forming the neck 106 integral to the handle 102 at the end 110 of the handle 102. In another embodiment, the neck 106 is detachable from the handle 102 at the end 110 of the neck 106. In this embodiment, the combined neck 106 and head 120 can be removed from the handle 102 to permit cleaning, servicing and/or replacement of the head 120. When the neck 106 is detachable from the handle 102, the first neck end 112 can include a connector (not shown) that is adapted to be detachably joined to the handle 102 using known techniques.

It will further be appreciated that the illustrated shapes of the handle 102 and neck 106 are merely exemplary in nature and the handle 102 and/or neck 106 can be formed to have any number of shapes. Preferably, the shapes of the handle 102 and the neck 106 are ergonomically pleasing to a user of the toothbrush 100 and provide a toothbrush which is easily gripped and held, and easily manipulated by the user. For example, the handle 102 can include slightly recessed finger sections 118 which are formed on opposite sides of the handle 102. One recessed finger section 118 can be designed to receive the thumb of one hand and the other recessed finger section 118 can be designed to receive one or more other fingers of the same hand to thereby assist the user in proper placement of the toothbrush 100 in the user's hand. One or more of the recessed finger sections 118 can include ribs, knurls, or another type of roughened surface to assist the user in gripping the toothbrush in the recessed finger sections 118.

The head 120 of the toothbrush 100 includes a head base 160 that partially defines an inner compartment 121 of the head 120. The head base 160 can be constructed so that it terminates in a rounded distal end 162, which actually defines the distal end of the toothbrush 100. Preferably, the head base 160 is integrally attached to the second end 114 of the neck 106.

The head 120 also includes a first movable bristle carrier 180 which is illustrated as being at the outermost or distal portion of the head 120. The first bristle carrier 180 can have a construction which is either identical to or similar to that of the bristle holder 13 illustrated in FIGS. 1A–1C. The first movable bristle carrier 180 may be configured as a disk of circular cross-section and mounted to the head base 160 in a manner such that it can freely be moved in an oscillating or rotating manner. However, it will be appreciated that the first movable bristle carrier 180 is not limited to having a disk shape and can have any number of different shapes, such as an oval or various other regular or irregular shapes, so long as the bristle carrier 180 can oscillate in a rotational manner. A circular shape is preferred since it requires the least amount of clearance to accommodate the oscillating movement.

A plurality of tooth care elements are coupled to and extend outwardly from the first movable bristle carrier 180. As used herein, the term "tooth care elements" includes any type of structure that is commonly used or is suitable for use in providing oral health benefits (e.g., tooth cleaning, tooth polishing, tooth whitening, massaging, etc.) by making intimate contact with surfaces of the teeth and surrounding areas. Such tooth care elements include, but are not limited to, tufts of nylon bristles that can be formed to have a number of different shapes and sizes and elastomeric members (see FIGS. 9–13) that can be formed to have a number of different shapes and sizes, or a combination of both. The arrangement of such tooth care elements is exemplified in the various figures attached hereto; however, it must be understood that an alternate arrangement may be preferred. Whatever particular arrangement of tooth care elements desired may be secured to the head by conventional means, including stapled or in-mold tufting (IMT) technology. Moreover, while the tooth care elements can be arranged so that they are generally perpendicular to the first bristle carrier 180, some or all of the tooth care elements can be angled at various angles with respect to the first bristle carrier 180.

While the first bristle carrier 180 has been defined as a movable bristle carrier 180, it will be understood that the first movable carrier 180 is not limited to having only tufts of bristles as a part thereof. Instead, the first movable carrier 180 is to be broadly considered as being a carrier for any number of suitable tooth care elements or any number of combinations of different types of tooth care elements. For example, the first movable carrier 180 can include a number of elastomeric members to provide the desired oral health benefits. The elastomeric members can be attached to the first movable carrier 180 using conventional techniques, including integrally molding the elastomeric members with an upper surface of the carrier 180. The tooth care elements provided as part of the first movable carrier 180 can thus be entirely of one type (e.g., bristle tufts or elastomeric members) or can be a mixed arrangement.

Figure 9:
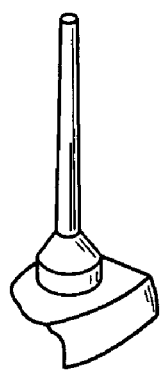
FIG. 9 is a perspective view of an elastomeric tooth care element having a first configuration and adapted for use in the toothbrush head.
Figure 10:
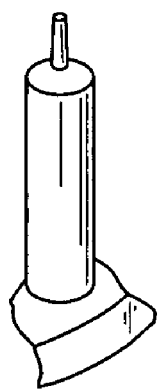
FIG. 10 is a perspective view of an elastomeric tooth care element having a second configuration and adapted for use in the toothbrush head.
Figure 11:
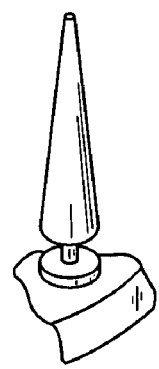
FIG. 11 is a perspective view of an elastomeric tooth care element having a third configuration and adapted for use in the toothbrush head.
Figure 12:
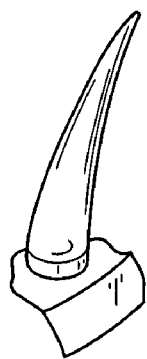
FIG. 12 is a perspective view of an elastomeric tooth care element having a fourth configuration and adapted for use in the toothbrush head.
Figure 13:
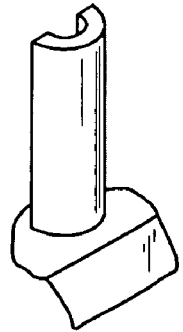
FIG. 13 is a perspective view of an elastomeric tooth care element having a fifth configuration and adapted for use in the toothbrush head.

FIGS. 9–13 illustrate various exemplary elastomeric members that serve as tooth care elements. FIG. 9 shows an elastomeric tooth care element in the form of a thin spike; FIG. 10 shows an elastomeric tooth care element in the form of a barrel spike; FIG. 11 shows an elastomeric tooth care element in the form of a squeegee point; FIG. 12 shows an elastomeric tooth care element in the form of an angled point; and FIG. 13 shows an elastomeric tooth care element in the form of a section of an elastomeric wall. The elastomeric wall of FIG. 13 can have a linear, planar shape; a zigzag shape; a serpentine shape; etc. All of the above elastomeric tooth care elements can have smooth textures or can have rough surfaces. In addition, the wall sections of the elastomeric tooth care elements can be vertically straight, taper toward inward toward one end or expand toward one end. The tops of the elastomeric tooth care walls can have a planar surface or can have a protrusion (i.e., hump) or the like formed thereat.

The toothbrush 100 includes a drive mechanism to effectuate movement of certain parts of the toothbrush 100 and more specifically, for causing movement of the first movable bristle carrier 180. One preferred drive mechanism is exemplified by that disclosed in U.S. Pat. No. 5,625,916 to McDougall, which has been previously incorporated herein by reference and includes a rotating drive shaft 200 that extends at least through the neck 106 (i.e., the inner compartment thereof). The drive shaft 200 preferably has a construction that is the same as or similar in nature to the shaft 12 illustrated in FIGS. 1A–1C.

The drive shaft 200 has one end (not shown) that is operatively connected to a drive member (not shown), such as a motor or any other type of drive device, for imparting movement to the first movable bristle carrier 180. The drive shaft 200 has an opposing distal end (not shown) that is bent such that the end is not axially aligned with the longitudinal axis of the drive shaft 200. This distal end can look similar to the end 20 of FIGS. 1A–1C or can be formed different so long as it performs the intended function. In other words, the end is an offset crank end of the drive shaft 200 and is configured to be received in the slot so that the 360° rotational movement of the shaft 200 is transmitted into an oscillating back and forth rotational movement of the first movable bristle carrier 180, an oscillating movement that may encompass an angle of between about 10° to about 120°, preferably about 10° to about 30°.

The drive mechanism for the powered toothbrush 100 can be any type of drive, e.g., a rotating drive, an oscillating drive, an eccentric drive, an unbalanced-generated drive, a drive having one more gearing mechanisms, and/or the like, that is capable of performing the intended function. The drive mechanism can be realized in the form of an electric motor or other type of motor and the movement generated by the drive can be imparted to one or more sections of the head 120 or to other elements that can be present at the brush section, such as bristle tufts, elastomeric members. The movement can be imparted directly through a driving axle, such as drive shaft 200, it can be imparted through a driving post attached to the driving axle, or by known means using a combination of bevel gears. When the toothbrush 100 includes an oscillating drive mechanism either identical to or similar to that illustrated in FIGS. 1A through 1C, the interior compartment of the handle 102 houses a motor operatively connected to the drive shaft 200 and a source to power the motor, such as one or more batteries.

Figure 3:
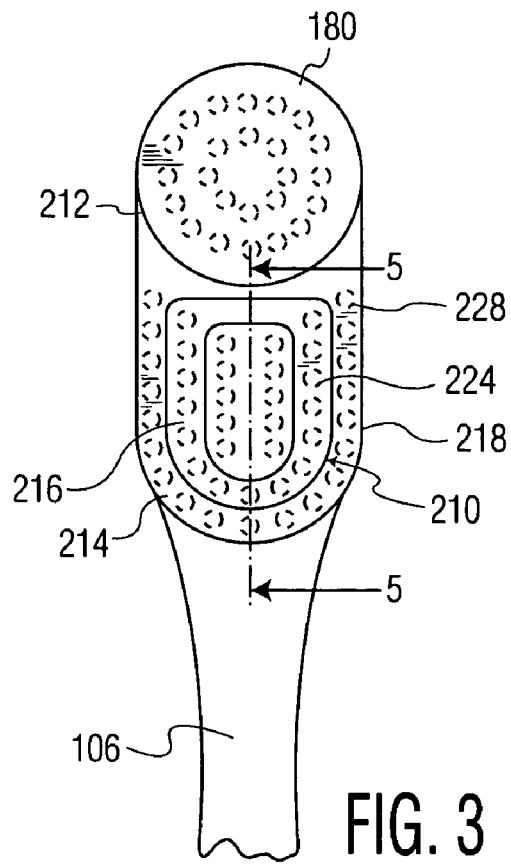
FIG. 3 is a front elevational view of the toothbrush head of FIG. 2.
Figure 4:
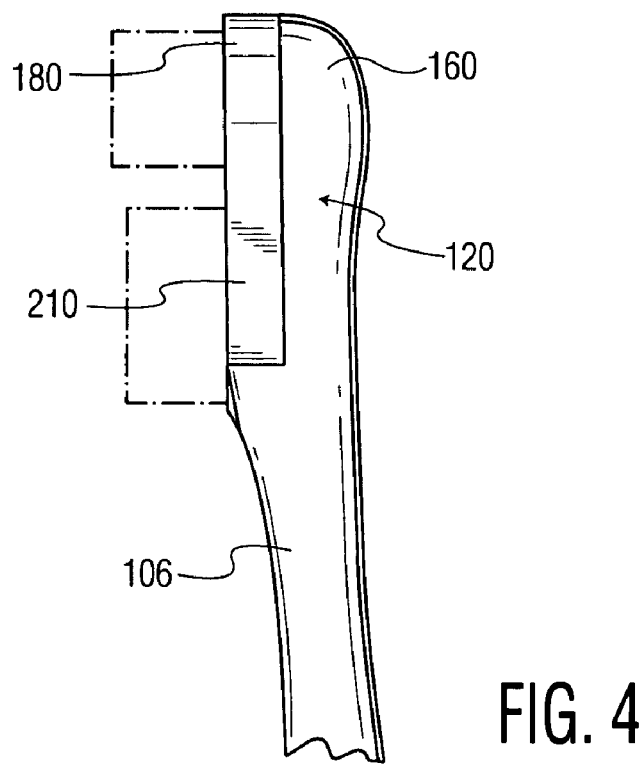
FIG. 4 is a side elevation view of the toothbrush head of FIG. 2.

The toothbrush 100 further includes a second movable part 210 that is coupled to the head 120 by an elastomeric member formed of a rubber and/or elastomeric material or combination thereof. The second movable part 210 has a range of movement when forces are applied to it during normal operation and/or normal use of the toothbrush 100. As illustrated in FIG. 3, the second moving part 210 has a first end 212 that is disposed in close proximate relation to the first bristle carrier 180 and an opposing second end 214 that is disposed at or near neck 106 end of the head 120. The second moving part 210 further includes a first side 216 and a second side 218 with a recessed section 220, as shown in FIGS. 5 through 8, being formed between the first and second ends 212, 214 and the first and second sides 216, 218. The recessed section 220 forms a recessed compartment that has a floor 222, also shown in FIGS. 5 through 8. A top face 224 of the elastomeric supported second bristle carrier 210 preferably includes the first and second ends 212, 214 and the first and second sides 216, 218 and preferably, the floor 222 is contained within a plane that is parallel to but offset from the plane containing the top face 224.

According to one exemplary embodiment, the second moving part 210 is only supported at the first side 216 and the second side 218, respectively, by the head base 160 such that the second moving part 210 extends across the inner compartment 121 of the head 120 and is substantially in the form of a "floating" elastomeric platform. The attachment joint of the second moving part 210 to the head base 160 can be accomplished using conventional techniques, such as using a hot or cold adhesive, providing a mechanical bond, or integrally attaching the two members during a molding operation, preferably a combination of these methods will be used, such as using both a mechanical and a molded bond. Use of a combination of a mechanical and molded bond will provide a stronger joint between the second moving part 210 and head base 160 that will reduce the chance of failure when the toothbrush 100 is in use. Because the first bristle carrier 180 is preferably in the shape of a disk, the first end 212 preferably has an arcuate shape to accommodate the oscillating back and forth rotational movement of the first bristle carrier 180. The second end 214 can also have an arcuate shape, as illustrated, or it can have any other shape. The second end 214 preferably forms a butt joint with the distal end of the neck 106 or the second end 214 can extend slightly over the distal end of the neck 106 if additional support of the second end 214 is desired.

A second bristle carrier 230 is securely disposed within the recessed section 220 of the second moving part 210 and is designed to hold a number of tooth care elements, such as a field of individual bristles, bristle tufts, elastomeric members or a combination thereof. Accordingly, the shapes of the second bristle carrier 230 and the recessed section 220 must be complementary to one another. In the illustrated embodiment, each of the second bristle carrier 230 and the recessed section 220 has a rectangular shape. However, other shapes can be used, such as a diamond, triangle, circle, square, or a polygon. The second bristle carrier 230 supports one or more and preferably a plurality of tooth care elements, generally illustrated at 250, which extend outwardly therefrom. The second bristle carrier 230 is preferably a relatively rigid member that is formed of a suitable material, preferably a plastic, such as a polyolefin, including polypropylene or polyethylene, that will provide the desired structural characteristics. However and according to an alternative embodiment, the second bristle carrier 230 is formed of an elastomeric material that can have a rigidity less than, equal to, or greater than the rigidity of the elastomeric material forming the elastomeric second bristle carrier 210.

The elastomeric supported second moving part 210, including the second bristle carrier 230, can be formed using conventional manufacturing methods. In one embodiment, the elastomeric second moving part 210 is formed around the second bristle carrier 230 in a conventional molding process where the second bristle carrier 230 is first positioned and properly located within a mold and then elastomeric material is injected around the second bristle carrier 230 to thereby form the elastomeric support for the second moving part 210 around the second bristle carrier 230. The second bristle carrier 230 which may also be injection molded, may be molded with thin extensions protruding from the surfaces thereof which are adjacent to and contacting with the second bristle carrier 230, to increase the area being joined, to strengthen the joinder.

Figure 7:
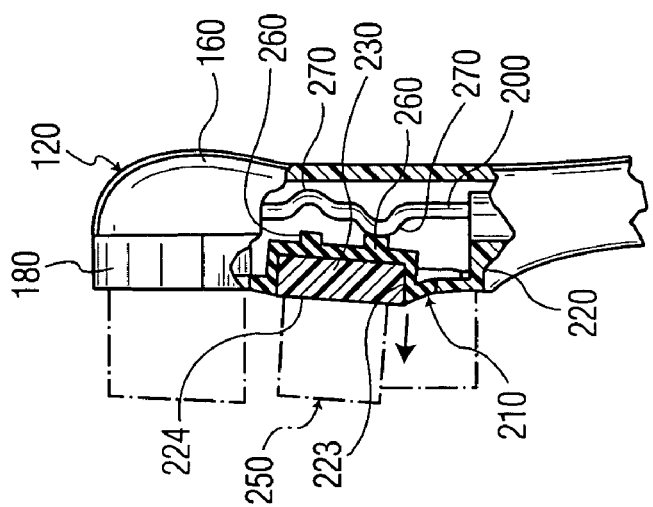
FIG. 7 is a side elevational view of the toothbrush head of FIG. 3 with parts broken away taken along the line 5—5 of FIG. 3 to illustrate the second movable section in a disturbed condition following the application of a force applied to the second movable section by the drive shaft.

On an underside 223 of the floor 222 of the elastomeric supported second moving part 210, one or more protuberances (protruding features) 260 or the like are formed. In the embodiment of FIGS. 3–7, there are two protuberances 260 (generally in the form of semi-circular nubs as shown in FIG. 7) that are spaced apart from one another and centrally located between the first and second sides 216, 218, respectively. The protuberances 260 are aligned above the drive shaft 200 that extends the length of the elastomeric second bristle carrier 210 underneath the floor 222 thereof.

Figure 1B:
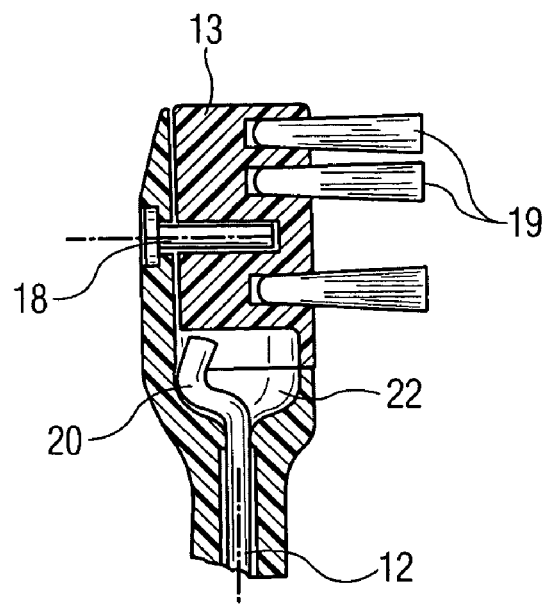
FIG. 1B is a partial cross-sectional side view of the toothbrush head of FIG. 1A.
Figure 1C:
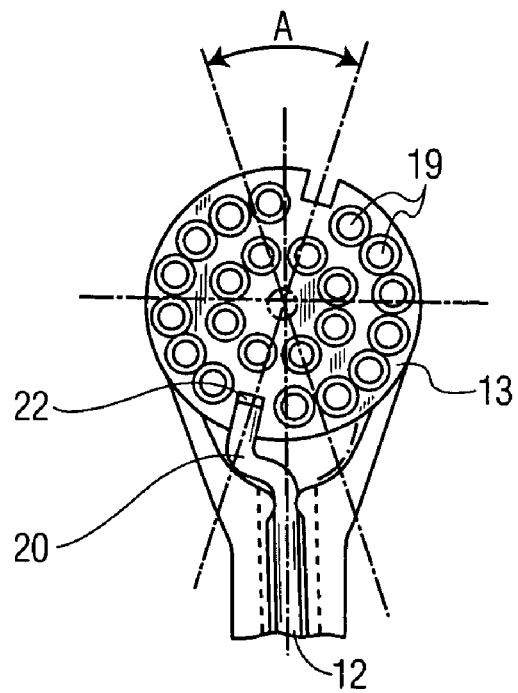
FIG. 1C is a partial cross-sectional front view of the toothbrush head of FIG. 1A.
Figure 2:
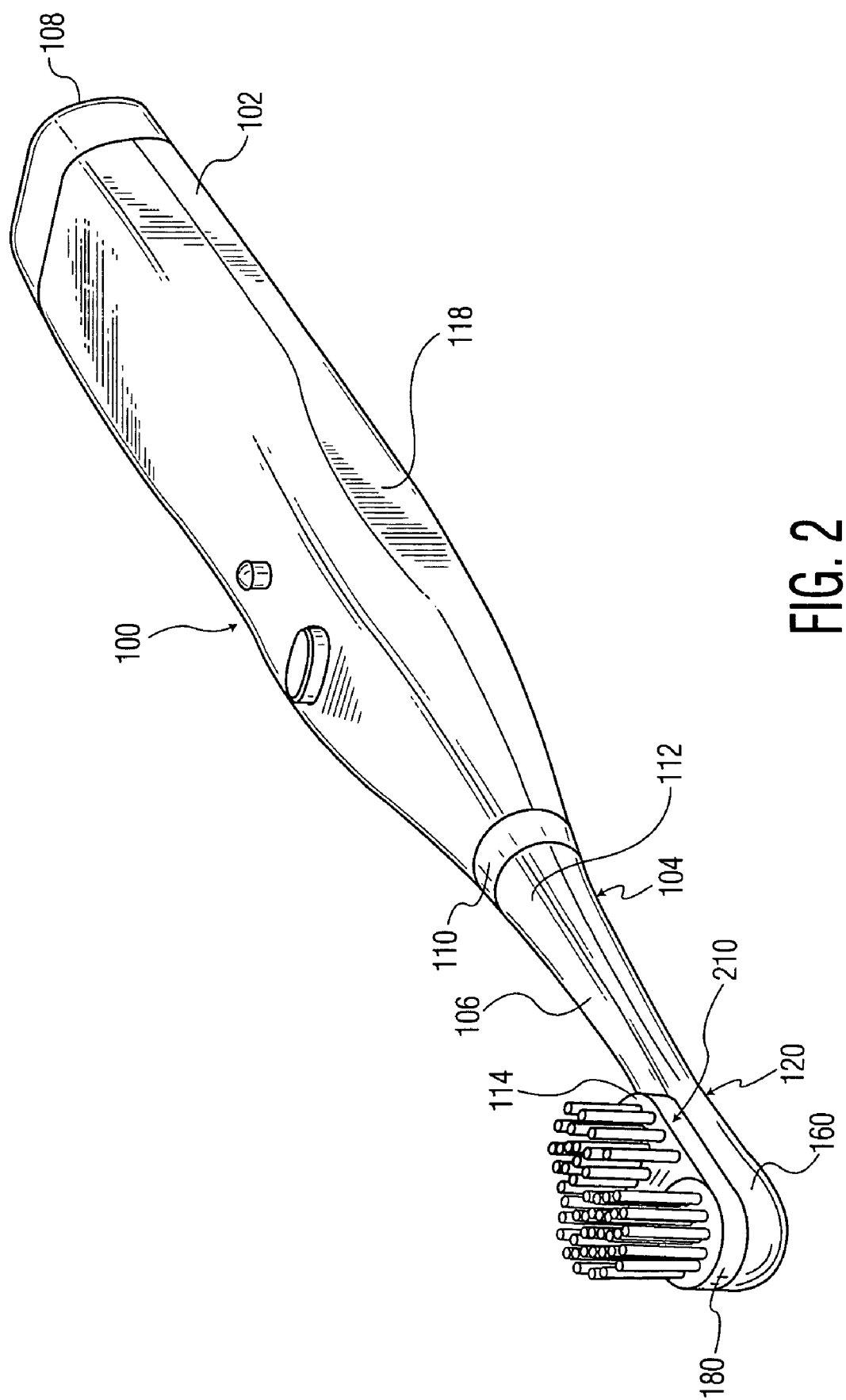
FIG. 2 is a front and side perspective view of a powered toothbrush according to one exemplary embodiment showing a toothbrush head having distinct first and second movable sections.

The drive shaft 200 differs from the drive shaft 12 of FIGS. 1A–1C in that it is formed to include at least one cam surface 270 along a length thereof for selectively contacting one or more of the protuberances 260. In the illustrated embodiment, the drive shaft 200 includes two cam surfaces 270, one for selectively contacting each protuberance 260 as the drive shaft 200 is rotated. The cam surface 270 has to be sufficiently displaced from the plane containing the longitudinal axis of the drive shaft 200 such that a top portion of the cam surface 270 contacts a portion of the protuberance 260. Because the exemplary embodiment contains two spaced protuberances 260, the drive shaft 200 includes two cam surfaces 270 that are spaced a predetermined distance apart from one another such that upon rotation of the drive shaft 200, each of the cam surfaces 270 contacts a respective protuberance 260. While the drive shaft 200 is illustrated as being the mechanism for driving both the first bristle carrier 180 and the second bristle carrier 230, it will be appreciated that two separate drive structures (e.g., two drive shafts) can be used to accomplish the above described movement of the first and second bristle carriers 180, 230.

While the two cam surfaces 270 can be formed such that they both contact the protuberances 260 at the same time, the illustrated embodiment shows the two cam surfaces 270 being formed such that the two cam surfaces 270 point in opposite directions. In other words, when the proximal-most cam surface 270 is pointed up, the distal-most cam surface 270 is pointed down. This results in the protuberances 260 being contacted at different times by the cam surfaces 270 as the drive shaft 200 is rotated.

Figure 6:
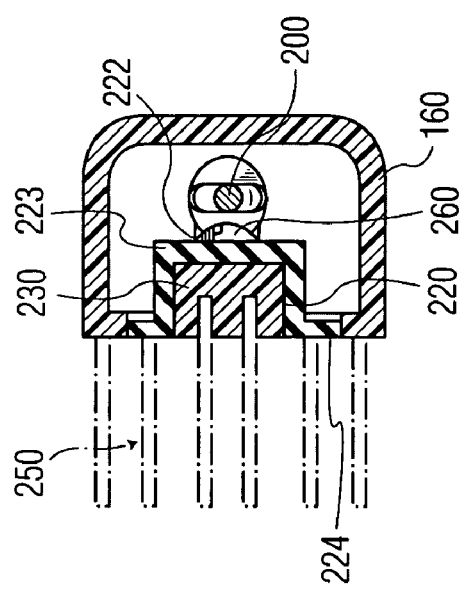
FIG. 6 is a cross-sectional view taken along the line 6—6 of FIG. 5.
Figure 5:
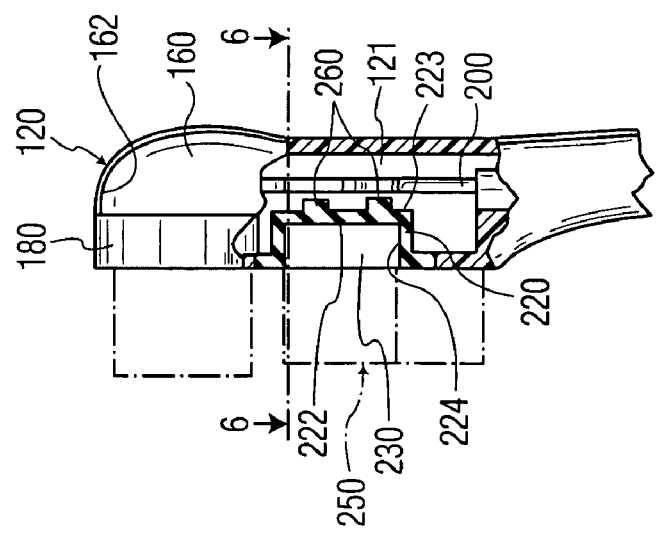
FIG. 5 is a side elevational view of the toothbrush head of FIG. 3 with parts broken away taken along the line 5—5 of FIG. 3 to illustrate the second movable section in a relaxed condition.

The action of the drive shaft 200 and more particularly, the cam surfaces 270 thereof, serves to impart movement to the second moving part 210. Because the second elastomeric supported bristle carrier 230 is a "floating" elastomeric platform within the second moving part 210, the striking action of the cam surfaces 270 against the protuberances 260 causes movement of the second bristle carrier 230. In the present embodiment, the action of the cam surfaces 270 causes the elastomeric supported second bristle carrier 230 to vibrate (i.e., move up and down). Moreover, by forming the cam surfaces 270 such that they point in opposite directions (180° apart), the ends 212, 214 are contacted by the cam surfaces 270 at different times and therefore, the second bristle carrier 230 vibrates in a rocking manner with the end 212 being moved up, while the end 214 is in a relaxed position, and then the end 214 is moved up after the end 212 has returned or is returning to its relaxed position. FIG. 6 shows the second end 214 being driven upwardly by the cam surface 270, while the first end 212 remains free of contact with the other cam surface 270. The elastomeric supported second bristle carrier 230 thus functions as a vibrating, oscillating platform as the first bristle carrier 180 is oscillating.

The vibration action of the second bristle carrier 230 deliver additional oral health care benefits like enhanced cleaning, tooth polishing, and/or tooth cleaning, since the second bristle carrier 230 has a number of tooth care elements 250 extending therefrom, which elements will move with the vibration of the second bristle carrier for enhanced contacting and massaging of the gingival surfaces during a brushing action. It will be understood that tooth care elements can be located in other areas besides the second bristle carrier 230. For example, some tooth care elements can be attached to and extend upwardly from the top face 224 of the second moving part 210 surrounding the second bristle carrier 230. In addition, in an embodiment where the sides 216, 218 of the second moving part 210 do not extend completely to the side edges of the head 120, tooth care elements can be disposed at these side edges of the head 120 adjacent one or more sides 216, 218 of the carrier 210 (as indicated in FIG. 3). Static tooth care elements can be disposed on other locations of the head 120 as well.

Figure 8:
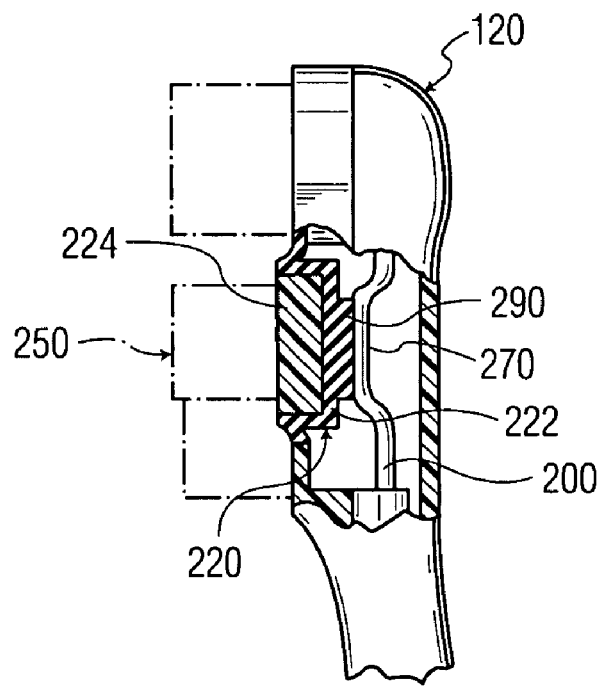
FIG. 8 is a side elevational view of a toothbrush according to another embodiment with parts broken away to illustrate an alternative second movable section in a relaxed condition.

FIG. 8 illustrates another embodiment where the drive shaft 200 includes only one cam surface 270 formed along a length thereof and the floor 222 has a single elongated ridge 290 formed on the underside 223. In this embodiment, the extended longitudinal length of the cam surface 270 and the ridge 290 causes a substantial longitudinal length of the carrier 210 to vibrate up and down when the cam surface 270 contacts the ridge 290.

Figure 14:
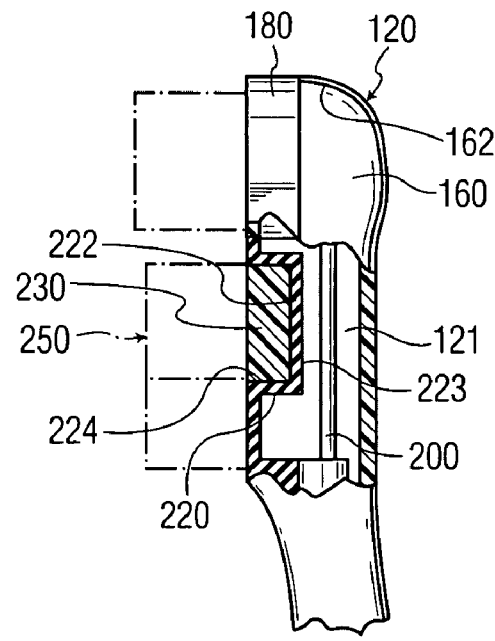
FIG. 14 is a side elevation view of a toothbrush according to another embodiment with parts broken away to illustrate an alternative second movable section in a relaxed condition.

FIG. 14 illustrates another and preferred embodiment of the present invention, in which the portion of the drive shaft 200 adjacent to the second elastomeric bristle carrier 210 is generally straight, i.e. does not have any type of cam surface, such as cam surface 270, and the second bristle carrier does not have any ridge extending from the floor 222 thereof, so that there will be no contact between the second moving part 210 and the drive shaft 200. The bristle holder 230, disposed within the recessed section 220 of the second moving part 210, will freely move both laterally and up-and-down, i.e. yield, within the second moving part 210 as forces are applied to the tooth care elements extending from the second bristle carrier 230 and transmitted to the unsupported second moving part 210, when the toothbrush 100 is in use and the tooth care elements are subjected to the normal forces involved in tooth brushing. This free, yielding movement of the second bristle carrier 230, will reduce the force being applied by the tooth care elements extending therefrom against the gums and other soft oral tissues to help in reducing wear thereof.

A powered toothbrush made in accordance with any of the present embodiments offers a number of advantages over conventional powered toothbrushes that are presently available. The movable first bristle carrier 180 oscillates back and forth, or moves otherwise, and as the operator brushes his or her teeth, the oscillating tooth care elements (i.e., bristle tufts and/or elastomeric members) contact the surfaces of the teeth and the surrounding areas to deliver enhanced cleaning, tooth polishing and/or tooth whitening. The second moving part 210 permits a number of additional tooth care elements to be disposed in a number of different patterns and the increased number of moving tooth care elements provides increased contact with gingival tissues and enhanced massaging thereof.

The toothbrush 100 according to the various embodiments disclosed herein can be made from any number of materials that are suitable for use in oral care products, such as toothbrushes, etc. For example, many of the components that are included in the toothbrush 100 are formed of plastic materials. Accordingly, the handle 102 and head 120 of the powered toothbrush 100 can be molded from polyolefins such as polypropylenes and polyethylenes, polyamids such as nylons, and polyesters such as polyethylene terephthalate.

Other suitable materials include polymethylmethacrylate, styrene acroylonitrate and cellulose esters, for example cellulose propionate.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide 2 or polyamide 6), polyesters (for example polyester ester or polyether ester), polyurethanes (for example polyesterurethane, polyetherurethane or polyesteretherurethane).

What is claimed is:

1. A head section for a powered toothbrush comprising:
   an outer surface,
   a fixed base portion,
   a first movable member from which at least one tooth care element extends, said first movable member being movable relative to said fixed base portion in a first direction,
   a second movable member comprising a carrier from which at least one tooth care element extends and an elastormeric member secured to said head, said elastomeric member extending beneath said carrier and forming a floating support platform for said carrier such that said carrier is movable relative to said fixed base section in a second direction; and
   a drive member that contacts a portion of said elastomeric member for moving said second movable member and said carrier in said second direction.

2. The head section of claim 1, wherein the second direction is different than the first direction.

3. The head section of claim 1, wherein said second moving part is coupled to side walls of the head section by said elastomeric member such that the second moving part extends transversely therebetween.

4. The head section of claim 1, wherein said first moving part rotates or oscillates back and forth in a direction generally parallel to the fixed base portion.

5. The head section of claim 1, wherein the second moving part has a lower surface having one or more protrusions formed thereon.

6. The head section of claim 5, wherein the second moving part moves in an up and down manner with respect to the fixed base portion.

7. A head section for a powered toothbrush comprising:
   a fixed base portion,
   a first movable member from which at least one tooth care element extends, said first movable member being movable relative to said fixed base portion in a first direction, and
   a second movable member comprising a carrier from which at least one tooth care element extends and an elastomeric member secured to said head, said elastomeric member includes a recessed portion tat extends beneath said carrier and in which said carrier is positioned, said elastomeric member forms a floating support platform for said carrier such that said carrier is movable relative to said fixed base section in a second direction.

8. The head section of claim 7, wherein the second direction is different than the first direction.

9. The head section of claim 7, wherein said first moving part rotates or oscillates back and forth in a direction generally parallel to the fixed base portion.

10. The head section of claim 7, wherein the second moving part has a lower surface having one or more protrusions formed thereon.

11. The head section of claim 10, wherein the second moving part moves in an up and down manner with respect to the fixed base portion.

* * * * *